United States Patent [19]

Kampner

[11] Patent Number: 4,840,632
[45] Date of Patent: Jun. 20, 1989

[54] HIP PROSTHESIS

[76] Inventor: Stanley L. Kampner, 2320 Sutter, San Francisco, Calif. 94115

[21] Appl. No.: 870,289

[22] Filed: May 21, 1986

Related U.S. Application Data

[63] Continuation of Ser. No. 590,258, Mar. 16, 1984, abandoned.

[51] Int. Cl.⁴ .............................. A61F 2/34; A61F 2/32
[52] U.S. Cl. ........................................ 623/22; 623/23; 623/18
[58] Field of Search ................... 128/927; 623/16, 17, 623/18, 19, 20, 21, 22, 23

[56] References Cited

U.S. PATENT DOCUMENTS

| | | | |
|---|---|---|---|
| 3,463,158 | 8/1969 | Schmitt et al. | 128/92 C |
| 3,543,749 | 12/1970 | Grove | 623/23 |
| 3,840,904 | 10/1974 | Tronzo | 128/92 C |
| 3,924,274 | 12/1975 | Heimke et al. | 128/92 CA |
| 3,987,499 | 10/1976 | Scharbach et al. | 128/92 CA |
| 4,068,324 | 1/1978 | Townley | 623/23 |
| 4,488,319 | 12/1984 | von Recum | 128/92 CA |
| 4,514,865 | 5/1985 | Harris | 128/92 CA |

FOREIGN PATENT DOCUMENTS

| | | | |
|---|---|---|---|
| 2621666 | 11/1977 | Fed. Rep. of Germany | 623/22 |
| 1446097 | 11/1976 | United Kingdom | 623/22 |

Primary Examiner—Richard J. Apley
Assistant Examiner—David J. Isabella
Attorney, Agent, or Firm—Townsend & Townsend

[57] ABSTRACT

Disclosed is a prosthetic hip joint defined by a femoral component and a cooperating acetabular component. The femoral component includes an intertrochanteric body which is press-fit into a correspondingly shaped intertrochanteric cavity at the top end of the patient's femur. Load transferring surfaces between the femoral implant and the femur are located within the intertrochanteric cavity and at the upper end of the femur. The load transferring surface are shaped to generate compressive stresses only. The femoral implant includes an attachable guide stem which can be resorbable and extends into the medullary cavity but which is not secured thereto to eliminate undesirable transference of stresses from the implant to the bone. The acetabular component is defined by an acetabular cup that is press-fit into a pre-reamed acetabular cavity in the patient's pelvis. An anchor bolt, which can be resorbable, is threaded into the pelvis, extends through a corresponding hole in the cup and is secured to the cup. A low friction insert, immovably attached to the interior of the cup, defines an acetabular socket which receives a cooperating ball on the femoral implant. The ball is secured to the femoral implant with a morse taper fit. Also disclosed is a procedure for implanting both components of the prothesis.

12 Claims, 4 Drawing Sheets

HIP PROSTHESIS

This is a continuation of application Ser. No. 590,258, filed Mar. 16, 1984, now abandoned.

BACKGROUND OF THE INVENTION

The prosthetic replacement of hip joints, either the acetabular component implanted in the patient's pelvis or the femoral component implanted in the femur, or both, is now widely practiced to replace degenerated natural hip joints. Prosthetic hip joints have evolved over the years from early, relatively crude models to current prostheses which closely duplicate the functions and motions of a natural joint. As a result, prosthetic hips have provided patients with increasing comfort, freedom of motion and an ability to lead nearly normal lives.

Although there have been problems with excessive wear between components of prosthetic devices which move with respect to each other, by and large the fixation of the prosthetic components to the patient's bone structure did and continues to represent the greatest difficulty. Early attempts to incorporate large fenestrations or openings in the implant components, which were thought to mechanically lock the implants to the bone by promoting the growth of bone through such openings, were soon discarded because they proved unsuccessful. With the event of tissue compatible acrylic cement, implants were increasingly cemented to the bone and this practice continues to be widely followed because, at least in the short term, it has proved to be highly successful.

However, the longevity of cemented implants suffers primarily as a result of the differences in the moduli of elasticity at bone/cement and the cement/implant interfaces. For certain patients a loosening of the implant takes place after a number of years of other wise successful use. This can be painful and frequently requires the replacement of the implant which is burdensome, expensive and can incapacitate the patient for significant periods of time.

In the recent past, attempts have again been made to enhance the longevity of prosthetic implants by supplementing the cement bond with at least a degree of direct bone-implant interlocking. This has been accomplished by providing porous implant surfaces which contact the bone tissue so that, after a typical ingrow period of several weeks, bone tissue grows into the pores and thereby forms a firm, mechanical connection. To achieve such bony ingrowth, it is necessary that any relative movements between the bone and the porous implant surfaces are prevented. Currently, cement continues to provide the necessary fixation of the implant.

In spite of the improvements and advances that have taken place, the fixation of the implant to the surrounding bone structure remains the source of most implant failures. It is believed that this results from both failures of the implant-bone bond and the stresses generated between the implant, the bone and/or the cement.

For example, femoral components of hip implants typically include elongated stems which extend into the medullary cavity of the femur and, depending on the particular technique employed, are bonded to the surrounding bone structure and/or a bone ingrowth into porous implant surfaces is attempted. The transfer of forces from the implant to the bone generates shear stresses which are not readily transferred, which tend to weaken the interface and, over time, are likely to destroy the connection.

In addition, the load carrying structure of the femur is unnaturally stressed because the transfer of forces takes place over the entire length of the implant stem extending deep into the medullary cavity. In contrast, the normal load transfer to the femur is from the top. As a consequence, the absence of proper stressing of the femur from the top when conventional femoral implants are utilized leads to stress shielding at the top and a resultant bone resorption in this upper region which, in time, can lead to implant and/or bone failures.

The acetabular components of prior art prosthetic hips are similarly deficient. First, the fixation of the acetabular cups within corresponding sockets in the patient's hip is difficult because of their semispherical shape. In almost all instances, the cups are bonded to the pelvis with cement which, at various points over the exterior surfaces of the cups, is subjected to compression, shear or both. Over time, such unequal stressing of the bond is likely to lead to mechanical failure.

Additionally, the semi-spherical shape of the acetabular cups makes it difficult to properly locate the cup in the socket and fix it. Attempts have been made to provide such cups with spikes or screws to mechanically lock them in position. However, as these are driven into the bone an uncontrolled and undesirable repositioning of the cups is almost impossible to prevent.

As with femoral components, attempts have been made to improve the fixation of acetabular hip joint components by forming them with porous exterior surfaces to promote bone ingrowth and thereby establish a mechanical interlock between the patient's natural bone and the implant. Since such bone ingrowth requires immediate rigid fixation of the implant, cement continues to be used widely for initially securing the implant to the bone. Moreover, in the past it was thought desirable to attain bone ingrowth over as large a surface area of the acetabular component as possible. This results in bone ingrowth that is partially subjected to shear stresses along the sides of the cup. This makes it not only difficult to obtain bony ingrowth along the sides but can be harmful. If a bony ingrowth is obtained along the sides where shear stresses occur, there may occur an abnormal transference of stress to the top of the cup where most loading occurs in the natural state. The result will be stress shielding with resultant bone resorption about the top of the cup over a period of years, leading to potential mechanical failure of the device.

U.S. Pat. Nos. 4,068,324 and 3,840,904 are examples of recent developments and improvements in the construction of femoral and acetabular hip joint components.

SUMMARY OF THE INVENTION

As contrasted with the prior art, the present invention takes a fundamentally different approach to implanting prosthetic devices in general and the acetabular and femoral components of prosthetic hip joints in particular. Instead of increasing the surface areas of the components which contact the bone, such contact is limited to points where the transmission of forces generates substantially only compressive stresses. In addition, the need for a cement bond for the initial fixation of the implant is altogether eliminated. In its stead, the implants are mechanically fixed to the surrounding bone so that, even without cement, the implants are completely immovable from the moment of implantation.

As a result, the prosthetic hip of the present invention can be used full weight bearing by the patient from the very beginning, including the typical 6 to 8-week time period for adequate bone ingrowth into porous surfaces of the implants.

To this end, the present invention provides separate femoral and acetabular components of a prosthetic hip joint which can be implanted and used separately or in combination. In addition, the present invention provides a procedure for implanting the components without the use of cement. This latter aspect in and of itself enhances the longevity and reliability of the implant. Failures as a result of differences in the modulus of elasticity between the bone and cement and between the cement and the implant are significantly reduced because there are only two materials, namely the implant and the bone, which have differing moduli of elasticity.

More importantly, the present invention provides a prosthetic hip implant in which the transmission of forces between the bone and the implant generates substantially only compressive stresses and, at worst, generates only insignificant shear stresses. Additionally, the implant is constructed so that the bones, both the pelvis and the femur, are stressed in a manner which closely resembles their physiological stressing by a natural, healthy hip joint. Accordingly, both bone degeneration, due to unnatural stressing, and implant failures, due to a loosening of the implant, are substantially reduced or eliminated.

Addressing first the acetabular component of the implant of the present invention, it employs an anchor which is immovably fixed, e.g. screwed into the pectineal line of the patient's pelvis which protrudes into an acetabular cavity of the pelvis that was prereamed to a diameter slightly, e.g. 1 to 4 mm and preferably 1 to 2 mm smaller than the spherical diameter of the acetabular cup so that the cup must be press-fit into the cavity for an initial, firm contact. An end of the anchor extends into a corresponding hole in the cup, securely and immovably positions the cup in the cavity and biases the cup into firm contact with the bone to enhance bone ingrowth.

In one embodiment of the invention, the anchor has a head which directly engages the cup. In another embodiment, a separate screw is provided. It is disposed in the fixation hole of the cup and threadably engages the end of the anchor protruding into the acetabular cavity. It firmly compresses the cup into contact with the bone and firmly connects it to the anchor in the pelvis. In both embodiments, the cup is immovably fixed within the acetabular cavity from the very beginning. After bone ingrowth occurs about the surface of the cup, need for the anchor fixation is eliminated. Because of this, the anchor can be fabricated from resorbable biodegradable material, e.g., certain ceramics, such as calcium hydroxylapatite or tricalcium phosphate, polylactic acid, etc. as well as currently utilized non-absorbable metal and polymer materials. The end result is an acetabular component securely fixed to the pelvis by a bony ingrowth without evidence of the anchor system.

To assure the most efficient load transfer from the pelvis to the acetabular cup, the anchor is oriented at an angle of approximately 20° from the center line of femur. To promote efficient bone ingrowth and to limit it to areas where the ingrowth is subjected to substantially only compressive stresses, a portion of the exterior surface of the cup surrounding the anchor is porous. The remainder of the exterior surface is smooth to inhibit bone ingrowth and substantially prevent any unloading of stresses about the top of the cup, where compressive stresses occur.

The acetabular component also has a liner, constructed of a relatively low friction material. It is disposed within the cup and defines a generally semispherically shaped acetabular socket that engages a natural or artificial ball connected with the patient's femur.

The femoral component of the present invention has an intertrochanteric body which completely fills a correspondingly shaped, slightly undersize, pre-reamed intertrochanteric cavity formed in the proximal femur after its head and neck have been resected. The intertrochanteric body of the femoral implant defines at least one interior load transferring surface which is inclined about 70° from the longitudinal axis of the femur. In addition, the femoral implant preferably includes a similarly oriented exterior load transferring surface which engages a correspondingly inclined, planar face formed when the head and neck of the femur was resected. Thus, the load transfer between the femur and the femoral component takes place at the uppermost end of the femur. Consequently, the femur is stressed in a manner closely analogous to the physiological stressing of the femur in a normal hip. As a result, undesirable bone resorption and formation is substantially prevented.

The initial fixation of the femoral implant is purely mechanical by press-fitting the intertrochanteric body into the slightly undersized intertrochanteric cavity. In addition, the entire body, including the interior and exterior load transferring surfaces are porous to promote bone ingrowth and assure a firm, permanent fixation of the implant. The absence of cement, which is not needed because the tight fit immovably secures the implant to the bone, enhances a quick and thorough bony ingrowth into the porous surfaces.

The implant normally includes an elongated stem which extends downwardly into the medullary cavity. Its function is only to accurately guide and orient the femoral component during implantation. Load transfer from the elongated stem to the bone is eliminated in two ways. One method is to provide a smooth surface on a non-absorbable material, such as metal, polymer, ceramic, etc., to prevent bony ingrowth thus insuring the only fixation of the implant to bone being at the top in the intertrochanteric region, as is seen in the normal state. An alternative method is to utilize a resorbable biodegradable material, e.g., ceramic, polylactic acid, etc., for the stem which is fixed to the intertrochanteric body by threads or the like. This biodegradable resorbable material can be fabricated to resorb over any desired time period, allowing an adequate period of time to elapse for bony ingrowth about the intertrochanteric body portion. The end result is a stemless femoral component filling only the remaining neck and intertrochanteric region of the femur. This ensures a more physiologic stress transference to the femur. In this manner, undesirable shear stresses, and an unnatural loading of the femur (over the length of the stem) are prevented.

The femoral implant includes also a neck and a replaceable ball. A Morse taper on the neck and in a corresponding bore of the ball is utilized to immovably secure the ball to the neck. With such a connection, a supply of different size balls having extensions of varying lengths can be provided so that the size of the implant, and particularly the effective length of the neck can be adjusted to suit patients of differing sizes and having varying hip joint configurations. This results in a significant reduction in the number of femoral components that must be carried in inventory and, thereby substantially reduces costs.

The intertrochanteric body is defined by generally opposite and spaced apart anterior and posterior sides and generally opposite, spaced apart lateral and medial sides. The spacing between the lateral and medial sides decreases in a generally downward direction. The body has a pair of interior load transferring surfaces which are contiguous with the anterior and posterior body sides, face generally downwardly and are inclined about 70° to the longitudinal axis of the femur so that the applied loading forces act substantially perpendicular to the implant surfaces. Consequently, substantially only compressive forces are generated between the implant and the femur.

Lastly, the present invention includes procedures for the implantation of the acetabular and femoral components.

With respect to the acetabular component, the procedure provides that the acetabular socket in the pelvic bone of the patient be reamed to form a generally semi-circular acetabular cavity which is seized slightly smaller than the acetabular cup so that the latter is press-fit into the cavity. The cup is positioned in the cavity so that the fixation hole overlies the pectineal line of the pelvis. Following placement of a drill hole, the anchor is inserted through the bore into the pelvis and is immovably fixed to the pelvis. The cup is immovably connected to the free end of the anchor in a manner which enhances by compression the contact pressure between the cup and the bone and thereby promote bone ingrowth into the porous area of the exterior cup surface.

Lastly, the low friction insert is snapped into the cup and locked in place to form the acetabular socket for cooperation with a femoral component of the patient's hip joint.

With respect to the femoral component, the procedure of the present invention initially requires that the upper end of a femur be resected to expose the interior thereof. The intertrochanteric, upwardly open cavity is then shaped in the femur so that it has substantially parallel, spaced apart anterior and interior sides, a lateral side and a spaced apart medial side, and load transmitting, generally upwardly facing ledges at a lower end of the anterior and posterior sides which are angularly inclined relative thereto. The sides and ledges of the cavity are dimensioned to establish a press-fit with the cooperating sides and and interior load-transferring surfaces of the femoral component when the latter is implanted.

After formation of the cavity, the femoral implant is inserted into the femur by extending its resorbable or non-absorbable stem into the medullary cavity and pressing the intertrochanteric body into the intertrochanteric cavity to tightly seat the former in the latter. Lastly, the ball is secured to the neck of the femoral implant for placement into an acetabular socket.

DESCRIPTION OF THE PREFERRED EMBODIMENTS

Figures 1, 2, 5, 6:
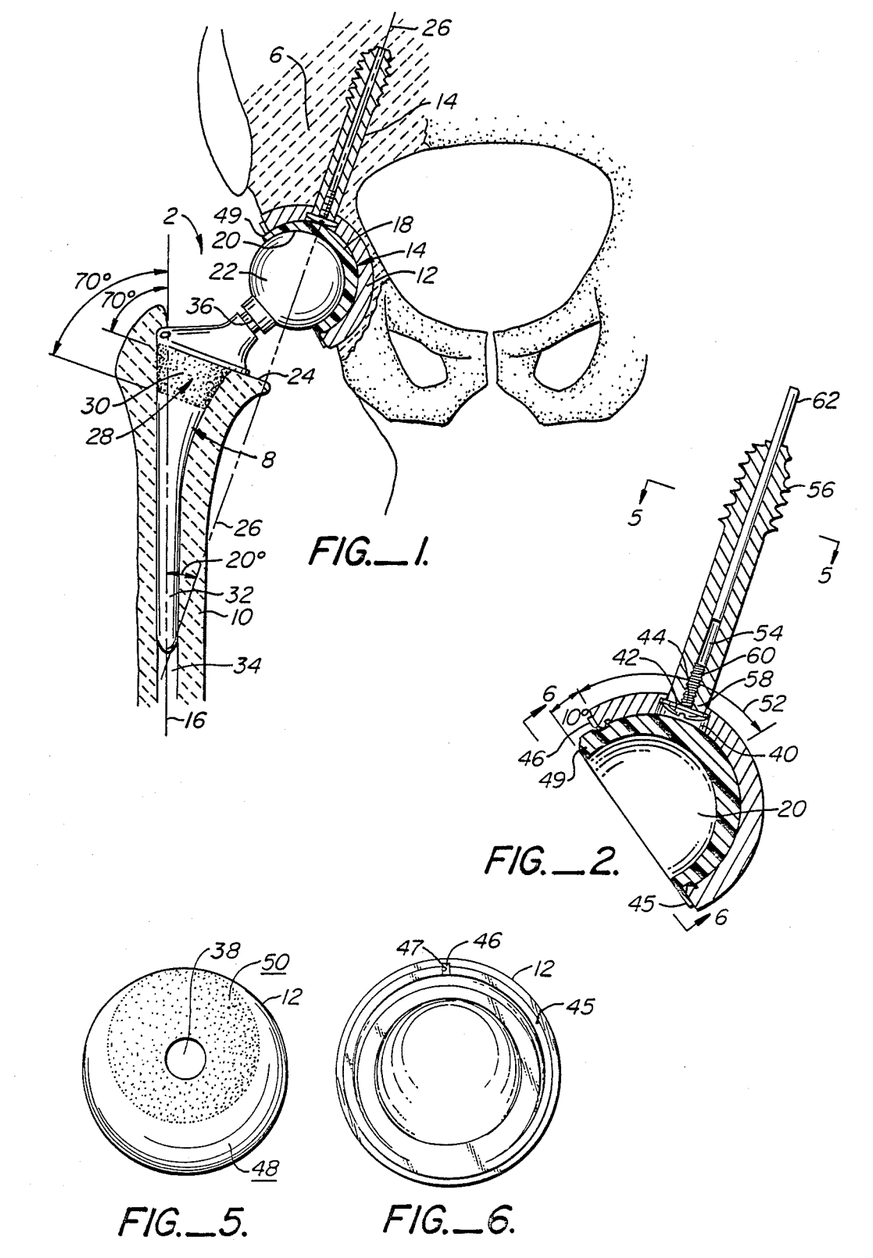
FIG. 1 is a schematic, front elevational view through a human hip joint, illustrates the pelvis and the upper portion of the femur, and shows a prosthetic hip constructed in accordance with the present invention.
FIG. 2 is an enlarged cross-sectional view of the acetabular component of the prosthetic hip illustrated in FIG. 1.
FIG. 5 is a plan view of the outer acetabular cup only and is taken on line 5—5 of FIG. 2.
FIG. 6 is an end view of the outer acetabular cup only and is taken on line 6—6 of FIG. 2.

Referring first to FIG. 1, a prosthetic hip 2 constructed in accordance with the present invention comprises an acetabular component 4 fixed to a patient's pelvis 6 and a femoral component 8 attached to the patient's femur 10. Broadly speaking, the acetabular component is defined by an acetabular cup 12 connected to an anchor bolt 14 threaded into the pelvis along the pectineal line at an inclination of approximately 20° relative to the longitudinal axis 16 of the femur. Disposed within the cup is a low friction liner or insert 18 which defines a spherically shaped acetabular socket 20 that moveably receives a ball 22 attached to the femoral implant 8.

To enable the implantation of to the femoral component 8, the head and neck of the femur 10 are initially resected to form an exterior femoral face 24 which is planar, generally perpendicular to the pectineal line 26 and, therefore, at an angle of approximately 70° to the longitudinal femur axis 16.

The femoral implant includes an intertrochanteric body 28 which is press-fit into a correspondingly shaped and appropriately dimensioned intertrochanteric, upwardly opening cavity 30 in the femur. A stem 32 extends downwardly from the body into the medullary cavity 34 of the femur. The femoral component further has a neck 36 on its medial side which extends generally upwardly and in a medial direction and to which is mounted the ball 22 that cooperates with the socket 20 of the acetabular component.

Referring now to FIGS. 1, 2, 5 and 6, the construction and implantation procedure for the acetabular component 4 is described in greater detail. The acetabular cup 12 has a substantially semi-spherical configuration, that is it typically extends over an arc of about 180°, although this may be increased or decreased as the need therefor may arise. The cup is constructed of a non-corroding, high strength material such as a cobalt-chromium alloy or a titanium alloy, for example. It includes a fixation hole or bore 38 which is positioned so that, upon implantation of the cup, the bore is aligned with the pectineal line of the patient's pelvis. The bore includes a recess 40 which defines an inwardly facing shoulder that, upon implantation, is engaged by a head 42 of a screw 44. The recess 40 has a sufficient depth to fully accommodate the screw head 42.

The liner 18 is disposed in the concavity of the cup 12 and is constructed of a suitable impact resistant, low friction material, such as plastic. To prevent relative movements between cup 12 and insert 18, a locking mechanism is provided, e.g. a protrusion 46 on the face of the cup which cooperates with a corresponding slot 47 in a flange 45 of the insert.

For purposes more fully described hereinafter, in a preferred embodiment of the invention the insert extends over an arc slightly, e.g. 10° larger than the arc over which the cup extends. The protrusion 46 on the cup and the slot 47 in insert flange 45 are positioned so that upon implantation the uppermost portion of the insert protrudes past the cup as is shown in FIGS. 1 and 2.

Cup 12 includes an exterior porous surface area 50 which surrounds bore 38 to promote bone ingrowth in the area of load transfer between the pelvis and the cup. To achieve the desired bone ingrowth, the pores are preferably of a size in the range of between about 250–450μ. The remainder of the exterior cup surface is smooth to inhibit bone ingrowth thereover. The exact dimensioning of the porous area 50 is not critical. In one embodiment it is generally circular and concentric with bore 38 and it extends to the upper end of the cup which is proximate the bore (as is illustrated by the arrow 52 in FIG. 2). For a cup having an exterior diameter in the range of between about 40 to 60 mm, the approximate diameter of the porous area will typically be in the range from about 25 to about 55 mm, although deviations therefrom are readily accommodated. It is of importance, however, that the porous area 50 does not extend over the portion of the exterior cup surface which is not loaded, that is the surface portion which lies primarily below an imaginary, approximately horizontal plane (not illustrated) through the cup when it is implanted. The porous area may either be raised, level with the remaining surface of the cup, or indented. The porous area may be continuous as in the form of discrete, separated but closely adjacent sections or islands.

To prevent any potential toxic effect of increased ion transfer as a result of the increased surface area about the porous surface 50, at least the porous surface area can be coated with a thin impervious layer, e.g., methylmethacrylate cement, carbon, calcium hydroxylapatite, tricalcium phosphate, etc. Such coatings are made commercially according to methods which are unknown to applicant and which applicant believes are maintained a trade secret.

Referring again to FIGS. 1, 2, 5 and 6, anchor bolt 14 is cannulated, i.e. it has a concentric center bore 54 which extends over its length. A first, inner end of the anchor has an external thread 56 formed o cut into and firmly engage the bone structure. The opposite, free end 58 of the bolt includes a hexagonal or slotted recess (not shown) for engaging the bolt with a hexagonal (Allen) wrench or a conventional screwdriver. The center bore has an internal thread 60 which is engaged by screw 44. The anchor bolt is constructed of a suitably corrosion resistant and high strength material and such bolts are commercially available from such companies as Zimmer, Biomet, Howmedica or Richards, for example. The anchor bolt may be fabricated from a resorbable material such as biodegradable ceramics, polylactic acid, etc. The material can be designed to resorb at a predetermined time. For most applications this will coincide with a time period sufficient to allow mature bony ingrowth about the cup for adequate mechanical fixation of the implant do the pelvis.

Turning now to the installation of the acetabular component, the surgeon initially prepares the pelvis for the receipt of the acetabular cup 12 by reaming out the natural acetabular socket with a tool (not shown) which has a spherical diameter slightly, e.g. 1–2 mm smaller than the exterior diameter of the cup that is to be implanted. To facilitate this procedure the surgeon is provided with a kit which includes a supply of acetabular cups of one or more external spherical diameters and one or more reaming tools which have spherical diameters slightly less than the diameter of the corresponding cup or cups.

The acetabular cup 12 is then pressed into the reamed out acetabular cavity so that fixation bore 38 is in substantial alignment with the pectineal line. Thereafter, he pinpoints the location and desired orientation of the anchor bolt axis through the fixation bore so that the anchor bolt will extend along the pectineal line into the pelvic bone, and a hole (not separately shown) for the anchor bolt is drilled.

To facilitate the drilling and prevent the drill from straying off the desired center line, a guide wire 62 can be initially forced into the pelvic bone in alignment with the desired anchor axis. The drilling operation is then performed with a cannulated drill (not shown) which extends over and is guided into the bone by the guide wire. Since the anchor bolt is cannulated, the guide wire can remain in place or, optionally, it can be removed after the hole has been drilled.

Next, the anchor bolt is inserted through cup bore 38 and threaded into the drilled hole until the free end 58 of the bolt protrudes into the bore but ends short of the shoulder defined by the bore recess 40. Screw 44 is now tightened against the shoulder to firmly secure the cup to the anchor bolt and thereby compressing and increasing the contact pressure between the cup and the bone, particularly over the porous surface area 50 surrounding the fixation hole 38.

Figure 7:
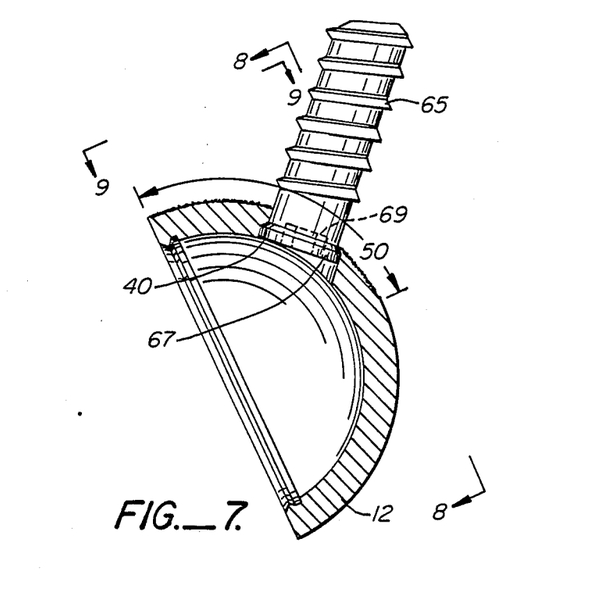
FIG. 7 is a view similar to FIG. 2 and shows another embodiment of the invention.

Finally, insert 18, properly oriented so that protrusion 46 and slot 47 are aligned, is snapped into the cup to thereby complete the implantation of the acetabular component. Referring momentarily to FIG. 7, the cup includes a radially inwardly extending ring 61 which engages a cooperating exterior groove 63 on the insert 18. The cup and the insert are suitably chamfered to facilitate the snap fastening of the insert to the cup.

After implantation, the insert is positioned so that an overhanging portion 49 protrudes beyond the cup as shown in FIGS. 1 and 2. This provides for a better seating of the associated ball over a wider range of motions and helps prevent accidental dislocations of the ball and the socket.

Figure 8:
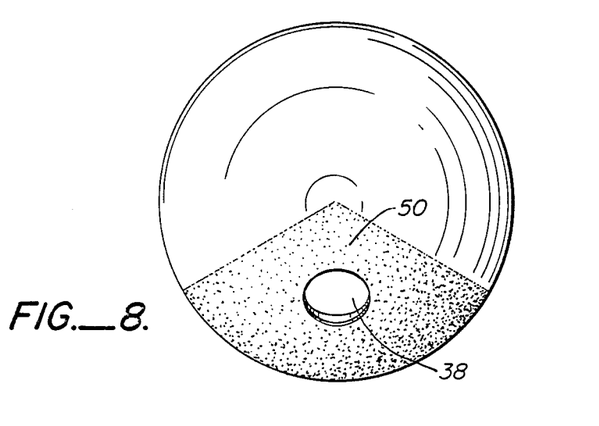
FIGS. 8 and 9 are end and side views, respectively, of the acetabular cup only shown in FIG. 7 and are taken along lines 8—8 and 9—9 of FIG. 7.
Figure 9:
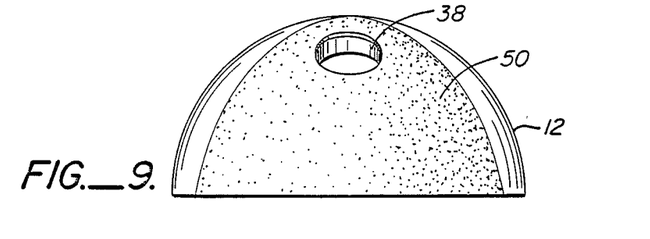

Referring now to FIGS. 7–9, in another embodiment of the invention, the acetabular cup 12 is constructed as previously described. However, this embodiment differs in the manner in which the cup is implanted. Instead of providing an anchor bolt-screw combination (as shown in FIGS. 1 and 2) to connect the cup to the anchor and increase the contact pressure between the exterior cup surface and the bone, an anchor bolt 65 is provided. It includes an integrally constructed head 67 which is disposed in fixation hole 38 and rests against bore recess 40. The cup illustrated in FIG. 7 includes the above-described rough exterior surface finish or porous area 50 which defines the bone ingrowth promoting, porous surface portion of the cup.

This embodiment of the invention is implanted by first pressing the cup into the acetabular cavity and the drilling anchor hole as was described above. Thereafter, the anchor is threaded into the drilled hole until its head 67 engages the bore recess 40. The anchor bolt is tightened to establish a firm connection between the cup and the anchor bolt and to compress and increase the contact pressure between the cup and the bone. A hexagonal slot 69 is preferably formed in the anchor bolt for a convenient tightening thereof.

Figure 3:
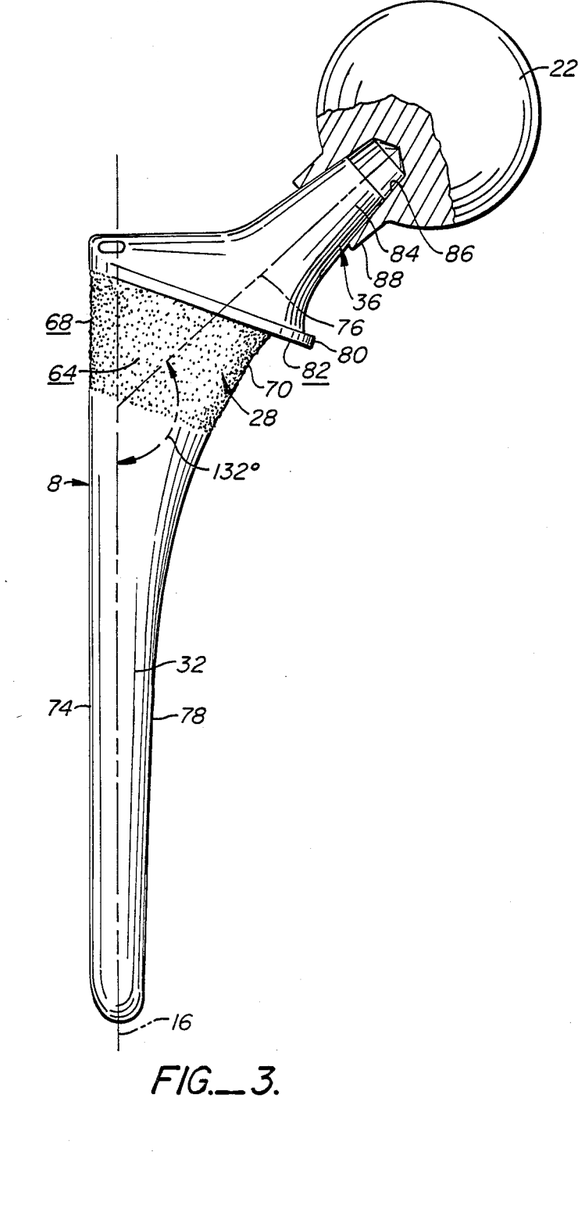
FIG. 3 is a front elevational view of the (right hand) femoral component of the prosthetic hip illustrated in FIG. 1.
Figure 4:
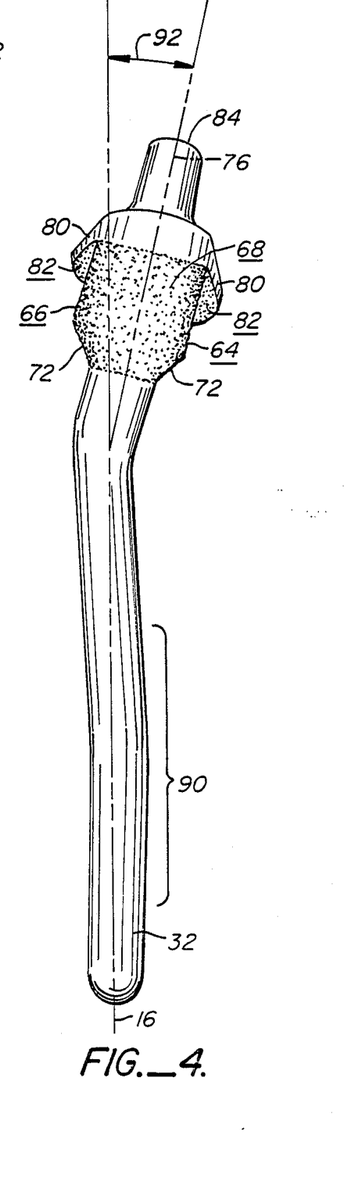
FIG. 4 is a lateral side elevational view of the femoral component shown in FIG. 3.

Referring now to FIGS. 1, 3 and 4, the construction and implantation procedure for the femoral component 8 is discussed in detail. The intertrochanteric body 28 forms the principle connection of the femoral component to the patient's femur. It is defined by an anterior side 64 and a spaced apart, posterior side 66, a lateral side 68 which extends laterally between the anterior and posterior sides, and a medial side 70, which extends medially between the anterior and posterior sides. In addition, the body includes an interior load transferring surface 72 at the lowermost (innermost) end of the anterior and posterior sides 64, 66. Each load transferring surface extends from the corresponding body side towards the center of the body, so that it faces generally downwardly. In addition, it is angularly inclined relative to the femoral axis 16 by about 70° (as is illustrated in FIG. 1) so that each load transferring surface also slopes downwardly by about 20° in a medial direction.

The body 28 is shaped so that it occupies most of the intertrochanteric cavity 30, which is shaped as is further described below. The lateral side 68 is substantially flat and, in the preferred embodiment of the invention, lies on a substantially straight line with the lateral portion 74 of the stem. The medial side 70 of the body is generally parallel to the neck axis 76 which, in the preferred embodiment of the invention, is at an angle of approximately 132° as is illustrated in FIG. 3. The medial side is generally planar from its upper end to about the interior loading surface 72. There is a concave, arcuate transition between the medial side 70 and the medial portion 78 of the stem forming a smooth line composed of an upper curved part forming the arc of circle of approximately a 10 centimeter radius and a lower rectilinear part. The stem itself has no function other than acting as a guide to ensure proper placement of the femoral intertrochanteric body and keep it there until bony ingrowth has fixed the body to the femur. The stem has a smooth surface to prevent bony ingrowth and ideally is of a smaller diameter than the medullary cavity of the femur in which it is inserted, so that there will be no abnormal transference of stresses to this area of femur.

Figure 10:
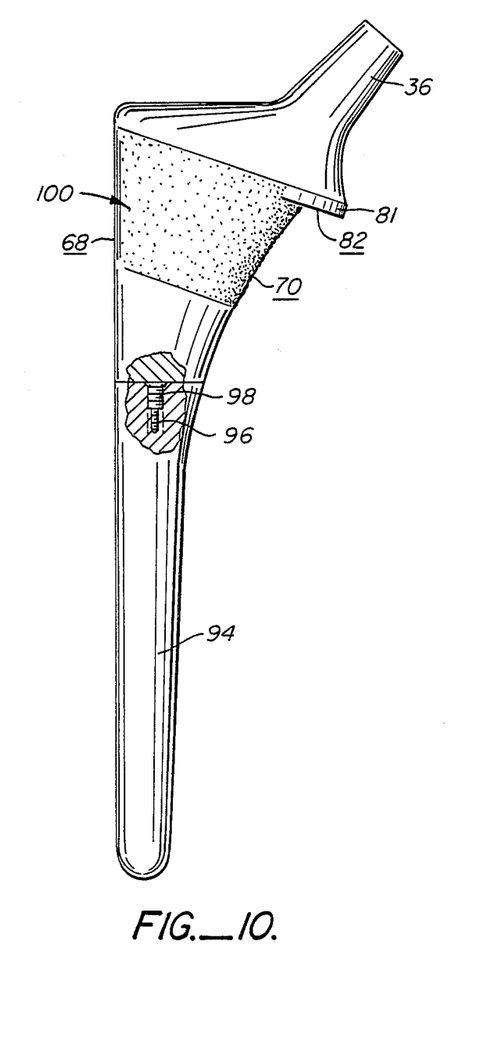
FIGS. 10 and 11 are views similar to FIGS. 3 and 4 and illustrate another embodiment of the invention.
Figure 11:
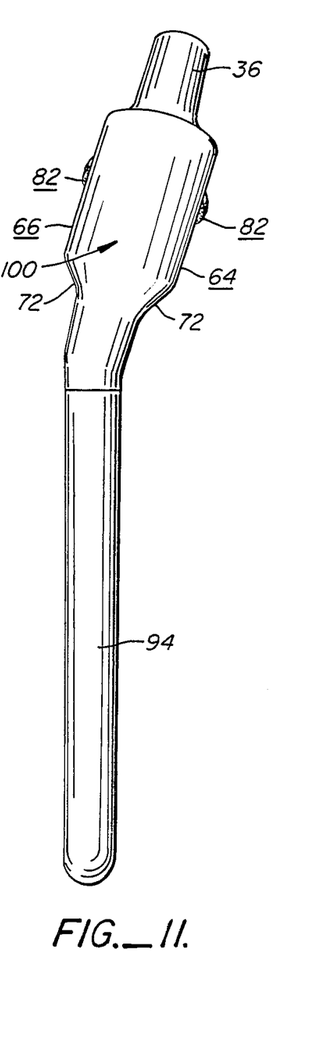

Referring momentarily to FIGS. 10 and 11, another embodiment of the invention utilizes a stem section 94 fabricated from a biodegradable or resorbable material which is connected to an intertrochanteric body 100, preferably with a female thread 96 on the stem which cooperates with a corresponding male thread 98 depending from the intertrochanteric body. Locating the female thread 96 in the stem section prevents the formation of stress concentrations in the body 100. Examples of biodegradable materials utilized for the stem section are polylactic acid, ceramics, etc. The interconnection between intertrochanteric body and the stem section 94 typically is in the region of the stem where it straightens out in the lateral plane (see FIG. 11), though, if convenient, it may also be located at other sites along the stem. Once the femoral implant is firmly fixed by bony ingrowth in its proper position, the function of the stem section is over and it can be eliminated by letting it resorb.

The final result is a stemless femoral component that allows a more physiologic transference of stresses to the proximal femur as opposed to a stemmed implant where there is the potential for fixation distally, thereby potentially causing stress shielding and bone resorption proximally with an increased chance of mechanical failure.

The stem has a round cross-section at its lower end which gradually becomes oblong as the medial side thereof slopes away from the stem axis towards the medial body side 70.

Referring to FIGS. 1, 3, 4, 10 and 11, in one embodiment (shown in FIGS. 3 and 4) all sides of the intertrochanteric body are porous (with a preferred pore size of between 200–450μ) to promote bone ingrowth. At least, however, the interior loading surfaces 72 are porous. It may be elected to leave the porous finish off of the lateral side 68 (see FIG. 11) and have only the three other sides 64, 66 and 70 porous, or both the lateral and medial sides 68, 70 may be left smooth, thus having just the anterior and posterior sides 64 and 66 porous.

The femoral component also has a loading flange 80 at the upper end of the intertrochanteric body 28 which protrudes generally perpendicularly past the anterior, posterior and medial body sides 64, 66 and 70 as shown in FIGS. 3 and 4. In an alternative embodiment, a loading flange 81 (see FIG. 10) protrudes only from the medial body side 70. In either embodiment, the flange defines a downwardly facing, external loading surface 82 which is parallel to the interior loading surface 72, that is which is at an angle of approximately 70° to the femur axis 16 and which slopes downwardly in the medial direction. The external loading surface of the flange is porous (like the sides of the body 28) and, upon implantation, rests firmly against face 24 of the femur.

The neck 36 of the femoral component extends upwardly in the medial direction from the loading flange 80 and includes an accurately machined end section 84 which defines a Morse taper. The ball 22 of the femoral component includes a cylindrical sleeve 88 and a bore 86 has a matching taper on neck end section 84 so that the ball can be firmly attached by pressing it onto the neck. This arrangement has the advantage that the effective length of the neck section of any given femoral implant can be adjusted as desired by providing a supply of balls 22 having varying cylindrical sleeve lengths and/or ball diameters. Inventory requirements are thereby substantially reduced and the surgeon has the ability to revise the neck length during implantation as may be required.

In a preferred form of the invention, the femoral implant is constructed so that it duplicates the natural shape of a femur as closely as possible. This requires the provision of both a left hand and a right hand femoral implant. Stems having a length of up to 130 mm are straight with respect to the lateral axis (see FIG. 11). Longer stems, e.g., having a length of 150 mm, preferably include an anterior bow which extends approximately over the bracketed length identified with the reference numeral 90 in FIG. 4 to better conform it to the shape of the medullary cavity. In one embodiment of the invention the anterior bow extends over an arc of about 4°.

Further, both the intertrochanteric body 28 (FIG. 4) or the body 100 (FIG. 11) and the neck 36 of the femoral implant have an anteversion angle 92 defined by an angular inclination of the body and the neck in the anterior direction of between about 7 to about 14°. Typically, the angle is approximately 10° from the femoral center line 16 as is illustrated in FIG. 4.

Turning now to the implantation procedure for the femoral component, the head and neck of the femur are first resected to form the external femoral loading face 24 (see FIG. 1). The intertrochanteric cavity 30 is then shaped by removing soft (non-load bearing) bone tissue with an appropriately shaped broaching tool (not shown). In this phase of the procedure, care must be exercised to assure that the shape, orientation and spacing of the cavity walls that correspond to the intertrochanteric body sides 66–70 and the interior loading surface 72 are such that, upon implantation, the exterior and interior loading surfaces 82, 72 simultaneously contact the corresponding bone surfaces. The entire intertrochanteric cavity is broached slightly undersize relative to the implant body to achieve a press-fit therewith.

Next, the femoral component is implanted by placing the stem into the medulary cavity and then pressing the intertrochanteric body 28 into the intertrochanteric cavity until the the internal and external loading surfaces 72, 82, firmly engage the bone. If a biodegradable stem is utilized at this stage, prior to implanting, the stem is connected to the intertrochanteric body by screwing it into the body. Alternatively, the interconnection may be made by screwing the intertrochanteric body into the stem.

During the implantation process the elongated stem acts as a guide which prevents an accidental misalignment of the intertrochanteric body during the insertion step, particularly when substantial forces must be applied to overcome the press-fit between the body and the cavity. Once inserted, however, the stem has no significant function. In particular, it is preferred that no firm contact exists between the femoral cortical bone and the stem (non-resorbable) to prevent any abnormal transference of stresses to the adjacent femoral bone. In the resorbable design with its resultant stemless implant, there are no distal stresses, as seen in the normal femur. The absence of such stresses about the femoral cortex adjacent to the stem, coupled with the transfer of loads at the loading surfaces 72, 82, assures that the femoral implant is top loaded in a manner analogous to the physiological loading of a femur in a healthy hip joint. Providing the stem with a smooth surface finish prevents the possibility of bone ingrowth.

Finally, the implantation procedure is completed by selecting a ball 22 of the appropriate diameter and with the appropriate length of its sleeve 88 and immovably securing the ball to the neck by firmly engaging the Morse taper connection between them.

I claim:

1. An acetabular implant for implantation in an acetabular cavity of a patient comprising a generally semi-spherical acetabular cup including a fixation hole positioned at a location spaced from an edge of the cup so that the hole can be substantially aligned with the pectineal line of the patient when the cup is implanted in the cavity, a portion of an exterior surface of the cup and at least partially spaced from the edge of the cup being porous to promote bone ingrowth upon implantation of the cup, the portion of the exterior cup surface extending over at least a part of the hole, a remainder of the exterior cup surface spaced from the hole and contiguous with at least a portion of the edge of the cup being substantially smooth to inhibit bone ingrowth, and an elongated anchor insertable into the pelvis for mechanically fixing the cup to the pelvis, the anchor including means for engaging the cup and applying a force to the cup in the direction of the anchor to thereby firmly seat the cup in the cavity.

2. The implant according to claim 1 wherein the portion of the exterior surface is defined by a plurality of indented surface sections, and wherein the surface sections are porous.

3. An implant according to claim 1 wherein the anchor is constructed of a resorbable material.

4. An acetabular implant for implantation in an acetabular cavity of a patient comprising a generally semi-spherical acetabular cup including a fixation hole positioned at a location spaced from an edge of the cup so that the hole can be substantially aligned with the pectineal line of the patient when the cup is implanted in the cavity, a portion of an exterior surface of the cup being porous to promote bone ingrowth upon implantation of the cup, the portion of the exterior cup surface extending over at least a part of the hole, a remainder of the exterior surface of the cup spaced from the hole being substantially smooth to inhibit bone ingrowth, an elongated anchor for insertion in the pelvis, the anchor including means for mechanically fixing the anchor to the pelvis so that a free end thereof communicates with the cavity, the hole being positioned on the cup so that it can be axially aligned with and placed over the protruding end of the anchor when the cup is placed into the acetabular cavity, and securing means extending through the hole and engaging the cup and the anchor for applying a force to the cup in the direction of the anchor to thereby firmly seat the cup in the cavity.

5. An implant according to claim 4 wherein the securing means comprises a screw member threadably engaging the anchor.

6. An implant according to claim 5 wherein the screw member has a head, and wherein the hole includes a recess dimensioned to receive the head.

7. An implant according to claim 4 wherein the mechanically fixing means includes an exterior thread adapted to threadably engage the pelvis and located at the ends of the anchor opposite the free end.

8. An implant according to claim 4 including an insert having a generally semi-spherical configuration adapted to be disposed in contact with an interior surface of the cup, the liner defining generally spherical acetabular socket.

9. An implant according to claim 8 including means preventing relative movement between the cup and the insert when the latter is disposed within the former.

10. An implant according to claim 9 wherein the insert extends over an arc greater than the arc of the cup so that a portion of the insert protrudes past the cup when disposed within the cup.

11. An implant according to claim 10 wherein the insert extends over an arc approximately 10° larger than the arc of the cup.

12. An acetabular implant comprising an elongated anchor having a first end disposed within and mechanically substantially immovably fixed to a portion of a pelvic bone of a patient and a free end extending in a generally downward direction into an acetabular cavity defined by the pelvis, the anchor being substantially aligned with the pectineal line of the pelvis; an acetabular cup disposed within the cavity and having a fixation hole spaced from an edge of the cup and aligned with the anchor, the free end of the anchor extending into the hole; a screw member disposed within the fixation hole, threadably engaging the anchor and demountably fixing the cup to the anchor, the cup having an exterior shape selected so that it generates a press-fit with the acetabular cavity, a portion of an exterior surface of the cup surrounding the hole extending over less than the entire exterior surface so that the portion is at least partially spaced from the cup edge, the portion being porous to facilitate bone ingrowth into such portion; a remainder of the exterior cup surface being spaced from the hole and substantially smooth to inhibit bone ingrowth; and a liner constructed of a material having a relatively low coefficient of friction disposed within the cup and defining a generally semi-spherically shaped acetabular socket engaging a ball member connected with the patient's femur.

13. A femoral implant adapted to be mechanically fixed to a femur with a pressfit between the implant and the femur comprising an intertrochanteric body adapted to be forced into an upwardly open intertrochanteric cavity previously formed proximate an upper end of the femur to correspond in shape to the shape of the body so as to establish intimate, pressfit contact between the body and the cavity, the body defining generally opposite and spaced apart anterior and posterior sides and generally opposite, spaced apart lateral and medial sides, a spacing between the lateral and medial sides decreasing in a generally downward direction, the body further defining an interior load transferring surface which is contiguous with at least one side, disposed generally below said one side and angularly inclined relative to said one side so as to face generally downwardly and being adapted to intimately contact a correspondingly formed surface of the femur for the transmission of compressive forces between the body and the femur via the load transferring surface, at least the interior loading surface including a porous area for promoting bone ingrowth when in contact with living bone; a neck protruding from the body and oriented to extend in a generally upward and medial direction; and a ball attached to the neck and formed to be movably disposed within a generally semi-spherical acetabular socket.

14. A femoral implant according to claim 13 wherein the interior loading surface is contiguous with at least one of the posterior and anterior sides of the body.

15. A femoral implant according to claim 14 wherein and interior loading surface is contiguous with both the anterior side and the posterior side of the body.

16. A femoral implant according to claim 13 including guide means connected with the body, depending generally downwardly thereof, and formed to extend into a medullary cavity of the femur for guiding the body into the intertrochanteric cavity during implantation of the implant in the femur.

17. A femoral implant according to claim 16 including means for detachably securing the guide means to the body.

18. A femoral implant according to claim 17 wherein the guide means is constructed of a biodegradable material.

19. A femoral implant according to claim 16 wherein the guide means comprises an elongated stem, and wherein the means for detachably securing comprises a threaded interconnection between the stem and the body.

20. A femoral implant according to claim 19 wherein the threaded interconnection is defined by a female threaded portion in the body and a male threaded portion on the stem.

21. A femoral implant according to claim 16 wherein the guide means comprises an elongated stem having a length substantially longer than the length of the body.

22. A femoral implant according to claim 21 wherein the stem has a smooth, non-porous surface to inhibit bone ingrowth.

23. A femoral implant according to claim 13 wherein the ball is separate of the neck, and means for immovably securing the ball to the neck.

24. A femoral implant according to claim 23 wherein the ball securing means comprises cooperating Morse tapers formed on the ball and on the neck.

25. A femoral implant according to claim 13 wherein the anterior and posterior sides each include a porous area for promoting bone ingrowth when in contact with living bone.

26. A femoral implant according to claim 25 wherein the medial side includes a porous area for promoting bone ingrowth when in contact with living bone.

27. A femoral implant according to claim 26 wherein the lateral side includes a porous area for promoting bone ingrowth when in contact with living bone.

28. A femoral implant according to claim 13 wherein the lateral side is smooth to prevent bone ingrowth when in contact with living bone.

29. A femoral implant according to claim 28 wherein the medial side is smooth to prevent bone ingrowth when in contact with living bone.

30. A femoral hip implant comprising an elongated stem disposed in a medullary cavity of a femur, the stem having a substantially smooth surface to inhibit bone ingrowth and extending upwardly towards an intertrochanteric cavity defined by walls of the femur and previously formed at an upper end of the femur; an intertrochanteric body integrally constructed with and disposed generally above the stem, tightly engaging walls defining the intertrochanteric cavity to thereby mechanically fix the body to the femur and having an anterior side and an opposite, spaced apart posterior side, a lateral side and an opposing, spaced apart medial side, the body further defining first and second spaced apart interior load transferring surfaces contiguous with the stem, the anterior side and the posterior side, respectively, and being angularly inclined relative to anterior and posterior sides, each interior load transferring surface facing generally downwardly and sloping generally downwardly in the medial direction at an angle of about 70° relative to longitudinal axis of the stem, at least the load transferring surface of the body being porous and in intimate contact with bone tissue to promote bone ingrowth into the porous sides and the surfaces; a neck extending upwardly from the body in a generally medial direction; and a ball immovably attached to the neck and movably disposed within a generally spherical acetabular socket on the patient's pelvis.

31. A femoral implant for implantation in a femur comprising an intertrochanteric body adapted to be forced into an upwardly open intertrochanteric cavity previously formed proximate an upper end of the femur for receiving and tightly engaging the body so as to mechanically fix the body and therewith the implant to the femur, the body defining generally opposite and spaced apart anterior and posterior sides and generally opposite, spaced apart lateral and medial sides, an interior load transferring surface formed to be in contact with a corresponding surface of the cavity and which is contiguous with and angularly inclined relative to at least one side for the transmission of compressive forces between the body and the femur via the load transferring surface and the corresponding cavity surface, the body also including a porous area for promoting bone ingrowth when in contact with living bone, a stem attached to the body for extending into the medullary cavity and constructed of a biodegradable material, and a ball attached to the body and formed to be movably disposed within a generally semi-spherical acetabular socket.

32. A prosthetic hip for a patient comprising an acetabular cavity including a generally semispherical acetabular cup including a fixation hole spaced from an edge of the cup and positioned so that the hole can be substantially aligned with the pectineal line of the patient when the cup is implanted in the cavity, a portion of an exterior surface of the cup being porous to promote bone ingrowth upon implantation of the cup, the portion of the exterior cup surface extending over at least a part of the hole, a remainder of the exterior surface of the cup which is spaced from the hole being substantially smooth, and an elongated anchor insertable through the hole into the pelvis for mechanically fixing the cup to the pelvis, the anchor including means for engaging the cup and applying a force to the cup in the direction of the anchor to thereby firmly seat the cup in the cavity, and a femoral implant for implantation in a femur including an intertrochanteric body adapted to be forced into an upwardly open intertrochanteric cavity previously formed proximate an upper end of the femur to correspond in shape and size to the body so as to tightly engage the body and thereby mechanically fix the body to the femur, the body defining generally opposite and spaced apart anterior and posterior sides and generally opposite, spaced apart lateral and medial sides, a spacing between the lateral and medial sides decreasing in a generally downward direction, the body further defining an interior load transferring surface which is contiguous with at least one side, angularly inclined relative to said at least one side and generally downwardly facing for the transmission of compressive forces between the interior load transferring surface and a correspondingly shaped and positioned surface of the femur, the sides and the interior loading surface including porous areas for promoting bone ingrowth when in contact with living bone; a neck protruding from the body and oriented to extend in a generally upward and medial direction; and a ball attached to the neck and formed to be movably disposed within and cooperate with the acetabular implant.

33. A procedure for the implantation of a femoral hip joint component comprising the steps of:
   (a) resecting the head and neck of a femur to expose the interior thereof;
   (b) shaping an intertrochanteric, upwardly open cavity in the femur which has substantially parallel, spaced apart anterior and interior sides, a lateral side and a spaced apart medial side and load transmitting, generally upwardly facing interior load transferring ledges at a lower end of the anterior and posterior sides which are angularly inclined relative thereto;
   (c) providing a femoral implant which includes an intertrochanteric body having anterior and posterior sides, a lateral side and a medial side, and interior load transferring surfaces for the transmission of compressive forces to the ledges which face generally downwardly and are contiguous with a lower end of the anterior and posterior sides, the sides and the interior load transferring surfaces being shaped complementary to the corresponding sides and the ledges of the cavity and dimensioned to tightly engage the intertrochanteric cavity, the femoral implant further including a downwardly extending, elongated stem;
   (d) inserting the femoral implant into the femur by extending the stem into the medullary cavity and pressing the intertrochanteric body into the intertrochanteric cavity to tightly seat the former in the latter whereby a compressive force applied to the femur and the implant is transmitted via the interengaged ledges and surfaces;
   (e) promoting the ingrowth of bone at an area where the body contacts the bone tissue;
   (f) inhibiting the ingrowth of bone over substantially full length of the stem; and
   (g) providing a ball on the femoral implant for placement into an acetabular socket.

34. A procedure according to claim 33 wherein the step of providing a ball comprises the step of providing a femoral implant having a neck; providing a separate ball; and securing the ball to the neck.

35. A procedure according to claim 34 wherein the neck defines a tapered shaft; the ball defines a correspondingly tapered bore; and wherein the step of securing comprises the step of frictionally engaging the ball with the neck to thereby immovably secure the two to each other.

36. A procedure according to claim 33 wherein the step of forming the intertrochanteric cavity includes the step of forming the ledges so that they slope downwardly in the medial direction at an angle of about 70° relative to the axis of the femur, whereby a force transmitted through the hip joint is transmitted from the surfaces to the ledges substantially perpendicularly thereto, whereby substantially only compressive stresses therebetween are generated.

37. A procedure according to claim 36 wherein the step of resection includes the step of resecting the head and neck of the femur to form an exterior load transferring face thereon which is contiguous with the intertrochanteric cavity, is oriented generally upwardly and is inclined at an angle of about 70° to the axis of the femur substantially parallel to the angular inclination of the ledge, and including the steps of contacting the face with a correspondingly shaped and oriented exterior load transferring surface on the implant, and promoting bone ingrowth over the exterior load transferring surface.

38. A procedure according to claim 37 wherein the step of promoting bone ingrowth comprises the step of forming porous surface on the implant over areas where bone ingrowth is desired.

39. A procedure according to claim 33 wherein the step of inhibiting comprises the step of providing the stem with a smooth surface finish.

40. A procedure according to claim 33 wherein the step of inhibiting comprises the step of permitting the stem to resorb.

* * * * *